United States Patent [19]

Shroot et al.

[11] Patent Number: 5,468,897
[45] Date of Patent: Nov. 21, 1995

[54] BI-AROMATIC ESTERS, A PROCESS FOR THEIR PREPARATION AND THEIR USE IN HUMAN OR VETERINARY MEDICINE AND IN COSMETIC COMPOSITIONS

[75] Inventors: Braham Shroot, Antibes; Jean-Michel Bernardon, Nice; William R. Pilgrim, Valbonne, all of France

[73] Assignee: Centre International de Recherches Dermatologiques Galderma (Cird Galderma), Valbonne, France

[21] Appl. No.: 237,991

[22] Filed: May 4, 1994

Related U.S. Application Data

[62] Division of Ser. No. 991,192, Dec. 16, 1992, Pat. No. 5,332,856, which is a division of Ser. No. 553,087, Jul. 17, 1990, Pat. No. 5,200,550.

[30] Foreign Application Priority Data

Jul. 18, 1989 [FR] France ................... 89 09652

[51] Int. Cl.⁶ .................... C07C 321/00; C07C 69/76
[52] U.S. Cl. .................... 560/18; 560/64; 560/65; 560/66; 560/55; 560/109; 560/76; 560/103
[58] Field of Search .................... 560/109, 18, 55, 560/64, 65, 66, 109, 76, 103; 514/533, 535, 539, 544

[56] References Cited

U.S. PATENT DOCUMENTS

| | | | |
|---|---|---|---|
| 2,958,705 | 11/1960 | Gordon | 560/109 |
| 3,335,164 | 8/1967 | Scherer | 560/109 |
| 4,000,144 | 12/1976 | Haas et al. | 260/294.8 |
| 4,481,149 | 11/1984 | Misaki et al. | 560/109 |
| 4,695,650 | 9/1987 | Walba et al. | 560/109 |

FOREIGN PATENT DOCUMENTS

| | | |
|---|---|---|
| 149754 | 7/1985 | European Pat. Off. . |
| 0232199 | 8/1987 | European Pat. Off. . |
| 1092932 | 11/1960 | Germany . |
| 2123175 | 12/1971 | Germany . |
| 8198463 | 11/1983 | Japan . |
| 1033146 | 2/1986 | Japan . |
| 1191270 | 5/1970 | United Kingdom . |
| 2200632 | 8/1988 | United Kingdom . |

*Primary Examiner*—Paul J. Killos
*Attorney, Agent, or Firm*—Cushman Darby & Cushman

[57] ABSTRACT

Bi-aromatic esters have the formula

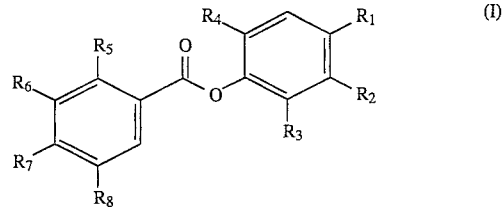

wherein $R_1$ represents H, OH, —$CH_3$, —$CH_2OH$, —CH(OH)$CH_3$, —COO$R_9$,

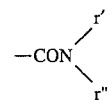

or SO$_2$R$_{10}$; R$_9$ represents H, C$_1$-C$_6$ alkyl or mono or polyhydroxyalkyl; R$_{10}$ represents OH, C$_1$-C$_6$ alkyl or

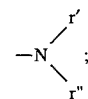

r' and r" represent H, C$_1$-C$_6$ alkyl, aryl, aralkyl, mono or polyhydroxyalkyl, or r' and r" taken together form a heterocycle; R$_2$ represents H, C$_1$-C$_6$ alkyl, OR$_9$, F or —CF$_3$; R$_3$, R$_4$ and R$_5$ represent H, F, OH, —CH$_3$, —OCH$_3$, —CF$_3$, —COOH or —CH$_2$OH; R$_6$ and R$_8$ represent H, α-substituted C$_3$-C$_{15}$ alkyl, α, α'-disubstituted C$_4$-C$_{12}$ alkyl, C$_3$-C$_{12}$ cycloalkyl, C$_5$-C$_{12}$ mono or polycyclic cycloalkyl whose linking carbon is trisubstituted, —SR$_{11}$, —SO$_2$R$_{11}$ or —SOR$_{11}$; R$_{11}$ represents C$_1$-C$_6$ alkyl or cycloalkyl; R$_6$ and R$_8$ cannot simultaneously represent H; R$_7$ represents H, C$_1$-C$_6$ alkyl, alkenyl, alkenyloxy, OR$_{12}$ or SR$_{13}$; R$_{12}$ represents H, C$_1$-C$_6$ alkyl or alkenyl; R$_3$ represents H, C1-C$_6$ alkyl or aralkyl; with the proviso that when R$_1$ represents

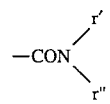

and R$_2$ represents H then: (i) either R$_3$ and R$_4$ are other than H or —CH$_3$, (ii) or R$_7$ is other than OR$_{12}$ and R$_6$ or R$_8$ is cycloalkyl having more than 7 carbon atoms, (iii) or R$_7$ is OR$_{12}$ but R$_6$ and R$_8$ are other than H, (iv) or R$_7$ is OR$_{12}$ but R$_5$ is other than H.

The bi-aromatic esters are employed in human and veterinary medicine and in cosmetic compositions.

20 Claims, No Drawings

BI-AROMATIC ESTERS, A PROCESS FOR THEIR PREPARATION AND THEIR USE IN HUMAN OR VETERINARY MEDICINE AND IN COSMETIC COMPOSITIONS

This is a division of application Ser. No. 07/991,192, filed Dec. 16, 1992, now U.S. Pat. No. 5,332,856, which is a division of application Ser. No. 07/553,087, filed Jul. 17, 1990, now U.S. Pat. No. 5,200,550.

The present invention relates to new bi-aromatic esters, to a process for their preparation and to their use in human and veterinary medicines and in cosmetic compositions.

These new bi-aromatic esters are also useful in the topical and systemic treatment of dermatologic ailments linked to a keratinization disorder (differentiation-proliferation) and dermatologic diseases, or others, having an inflammatory and/or immunoallergic component and in degeneration maladies of the conjunctive tissue. They also exhibit an antitumoral activity. Besides, these derivatives can be employed in the treatment of atophy, be it cutaneous or respiratory, and in rheumatoid psoriasis.

They are also useful in the ophthalmologic field, principally in the treatment of corneopathies.

The bi-aromatic esters in accordance with the present invention can be represented by the following formula

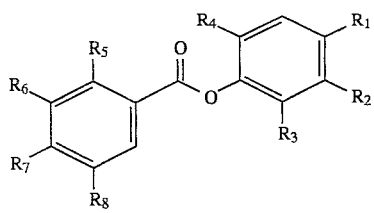

(I)

wherein $R_1$ represents hydrogen, OH, —$CH_3$, —$CH_2OH$, —$CH(OH)CH_3$,

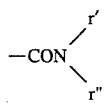

or $SO_2R_{10}$, $R_9$ represents hydrogen, alkyl having 1–6 carbon atoms, monohydroxyalkyl or polyhydroxyalkyl, $R_{10}$ represents OH, alkyl having 1–6 carbon atoms or

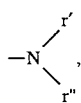

r' and r" represent hydrogen, alkyl having 1–6 carbon atoms, aryl, aralkyl, monohydroxyalkyl or polyhydroxyalkyl, or r' and r" together form a heterocycle, $R_2$ represents hydrogen, alkyl having 1–6 carbon atoms, $OR_9$, fluorine or —$CF_3$, $R_3$, $R_4$ and $R_5$ represent hydrogen, fluorine, OH, —$CH_3$, —$OCH_3$, —$CF_3$, —COOH or —$CH_2OH$, $R_6$ and $R_8$ represent hydrogen, —$CF_3$, α-substituted alkyl having 3–15 carbon atoms, α, α-disubstituted alkyl having 4–12 carbon atoms, cycloalkyl having 3–12 carbon atoms, mono- or polycyclic cycloalkyl having 5–12 carbon atoms whose linking carbon is trisubstituted or —$SR_{11}$, —$SO_2R_{11}$ or —$SOR_{11}$, $R_{11}$ represents alkyl having 1–6 carbon atoms or cycloalkyl, $R_6$ and $R_8$ cannot simultaneously represent hydrogen, $R_7$ represents hydrogen, alkyl having 1–6 carbon atoms, alkenyl, alkenyloxy, $OR_{12}$, $SR_{13}$, $SOR_{14}$ or $SO_2R_{14}$, $R_{12}$ represents hydrogen, alkyl having 1–6 carbon atoms, alkenyl, mono or polyhydroxyalkyl or —$(CH_2)_n$—$COR_{15}$, n being 0, 1 or 2 and $R_{15}$ representing hydrogen, OH, alkyl having 1–6 carbon atoms or alkoxy having 1–6 carbon atoms, $R_{13}$ represents hydrogen, alkyl having 1–6 carbon atoms or aralkyl, $R_{14}$ represents OH, alkyl having 1–6 carbon atoms or aralkyl, with the proviso that when $R_1$ represents —$CH_2OH$, —$CH(OH)CH_3$,

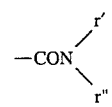

and $R_2$ represents hydrogen, then:
(i) either $R_3$ and $R_4$ are other than hydrogen or —$CH_3$,
(ii) or $R_7$ is other than $OR_{12}$ and $R_6$ or $R_8$ is cycloalkyl having more than 7 carbon atoms,
(iii) or $R_7$ represents $OR_{12}$, but $R_6$ and $R_8$ are then other than hydrogen,
(iv) or $R_7$ represents $OR_{12}$ but then $R_5$ is other than hydrogen.

The compounds in accordance with the present invention can also be provided in the form of salts when they have an acid function. It is then a case of an alkali metal salt, an alkaline earth metal salt or even zinc salts or organic amine salts.

By alkyl having 1–6 carbon atoms is meant, preferably, methyl, ethyl, isopropyl, butyl and tert.butyl.

By α-substituted alkyl having 3–15 carbon atom is meant isopropyl, 1-methyl propyl, 1-ethyl propyl, 1-methyl hexyl, 1-methyl decyl or 1-ethyl dodecyl.

By α,α'-disubstituted alkyl having 4–12 carbon atoms is meant principally tert.butyl, 1,1-dimethyl propyl, 1-methyl-1-ethyl propyl, 1-methyl-1-ethyl hexyl or 1,1-dimethyl decyl.

By monohydroxyalkyl is meant a radical having 2 or 3 carbon atoms, principally 2-hydroxyethyl, 2-hydroxypropyl or 3-hydroxypropyl.

By polyhydroxyalkyl is meant a radical containing 3–6 carbon atoms and 2–5 hydroxyl groups such as 2,3-dihydroxypropyl, 2,3,4-trihydroxybutyl, 2,3,4,5-tetrahydroxypentyl or the residue of pentaerythritol.

By alkenyl is meant a radical having 2–6 carbon atoms such as vinyl, allyl or 2-butenyl.

By aryl is meant phenyl optionally substituted by at least one halogen, hydroxyl or nitro function.

By aralkyl is meant benzyl or phenethyl optionally substituted by at least one halogen, hydroxyl or nitro function.

By cycloalkyl is meant cyclopentyl or cyclohexyl.

By mono or polycyclic cycloalkyl having 5–12 carbon atoms whose linking carbon is trisubstituted is meant 1-methyl cyclohexyl or 1-adamantyl.

When the r' and r" radicals taken together form a heterocycle, the heterocycle preferably is a piperidino, morpholino, pyrrolidino or piperazino radical, optionally substituted in the 4 position by a $C_1$–$C_6$ alkyl or a mono- or polyhydroxyalkyl such as defined above.

Representative compounds of formula (I) above include principally the following:

4-[3-(1-adamantyl)-4-methoxybenzoyloxy]-3-fluorobenzoic acid,
4-[3-(1-adamantyl)-4-methoxybenzoyloxy]-2-fluorobenzoic acid,
4-[3-(1-adamantyl)-4-methoxybenzoyloxy]-2-methylbenzoic acid,
4-[3-(1-adamantyl)-4-methoxybenzoyloxy]-2-hydroxybenzoic acid,
4-[3-(1-adamantyl)-4-methoxybenzoyloxy]-2-methoxybenzoic acid,
4-[3-(1-adamantyl)-4-methoxybenzoyloxy]-3-methoxybenzoic acid,
4-[3-(1-adamantyl)-4-methoxybenzoyloxy]-2-trifluoromethylbenzoic acid,
methyl 4-[3-(1-adamantyl)-4-methoxybenzoyloxy]-2-hydroxybenzoate,
4-[5-(1-adamantyl)-2-fluoro-4-methoxybenzoyloxy]benzoic acid,
4-[5-(1-adamantyl)-2,4-dimethoxybenzoyloxy]benzoic acid,
4-[3-(1-adamantyl)benzoyloxy]benzoic acid,
4-(3,5-di.tert-butyl-4-hydroxybenzoyloxy)benzoic acid,
4-[3-(1-adamantyl)-4-vinylbenzoyloxy]benzoic acid,
4-[3-(1-adamantyl)-4-ethylbenzoyloxy]benzoic acid,
4-[3-(1-adamantyl)-4-butylbenzoyloxy]benzoic acid,
4-[3-(1-adamantyl)-4-allyloxybenzoyloxy]benzoic acid,
4-[3-(1-adamantyl)-4-methoxybenzoyloxy]isophthalic acid,
4-[3-(1-adamantyl)-4-methoxybenzoyloxy]benzenesulfonamide,
4-hydroxyphenyl 3-(1-adamantyl)-4-methoxybenzoate,
phenyl 3-(1-adamantyl)-4-methoxybenzoate,
4-methylphenyl 3-(1-adamantyl)-4-methoxybenzoate,
4-[3-(1-adamantyl)-4-methoxybenzoyloxy]-3-hydroxymethyl benzoic acid,
4-[3-(1-adamantyl)-4-methylthiobenzoyloxy]benzoic acid,
4-[3-(1-adamantyl)-4-acetoxybenzoyloxy]benzoic acid,
4-[3-(1-adamantyl)-4-methylsulfonebenzoyloxy]benzoic acid,
4-[3-(1-adamantyl)-4-(carboxy methyleneoxy)benzoyloxy]benzoic acid,
4-[3-(1-adamantyl)-4-(2,3-dihydroxypropyloxy)benzoyloxy]benzoic acid, and
4-[3-(1-adamantyl-4-methoxycarbonylmethyloxy]benzoic acid.

The particularly preferred compounds of the present invention can be represented by the following formula

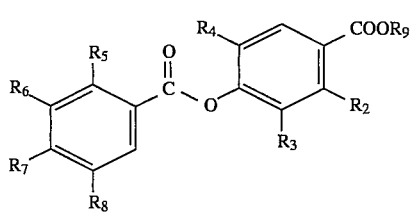

wherein
(i) either $R_3$ to $R_9$ have the same meanings defined above for formula (I) and $R_2$ represents alkyl having 1–6 carbon atoms, $OR_9$, fluorine or —$CF_3$,
(ii) or $R_2$ to $R_4$ and $R_6$ to $R_9$ have the same meanings given above for formula (I) and $R_5$ represents fluorine.

The present invention also relates to a process for the preparation of the Compounds of formula (I).

(a) When $R_1$ represents hydrogen or —$CH_3$, the compounds in accordance with the present invention can be prepared in accordance with the following reaction scheme:

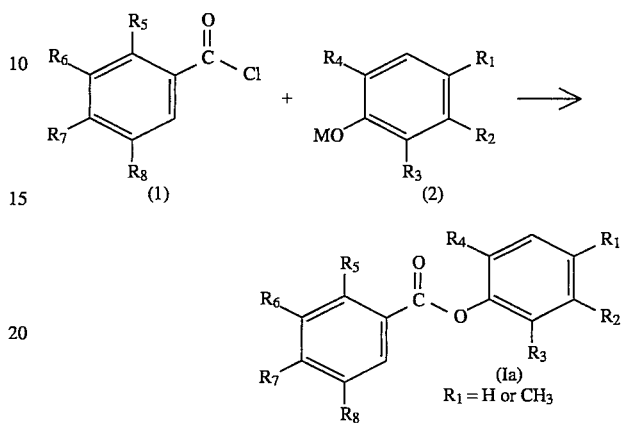

The principal step in this process resides in reacting in an anhydrous medium, in an organic solvent such as tetrahydrofuran or methylene chloride containing a tertiary amine (pyridine or triethylamin), or an alkaline hydride, such as sodium hydride, an activated form of a substituted benzoic acid, for example, an acid chloride (1), on a mixed anhydride, with a benzene compound having a hydroxy function para to the $R_1$ radical (2), the reaction being carried out at ambient temperature and with stirring.

(b) For the other meanings of $R_1$, the compounds are prepared by protecting $R_1$ by an allylic or benzylic type protective group. The synthesis to the free form can be carried out, in the case of an allylic protective group, by means of a catalyst such as certain complexes of a transition metal in the presence of a secondary amine, and in the case of a benzylic protective group, by debenzylation in the presence of hydrogen, by means of a catalyst such as palladium on charcoal. When $R_1$=OH the protective group preferably is benzylic. When $R_1$=—$CH_2OH$ or $CH(OH)CH_3$, it preferably is allylic. When $R_1$=$COOR_9$, it can be either allylic or benzylic, when $R_1$=COOH, the compounds of formula Ia can be prepared in accordance with the following reaction scheme:

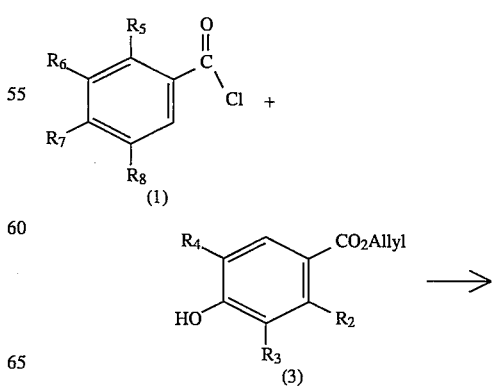

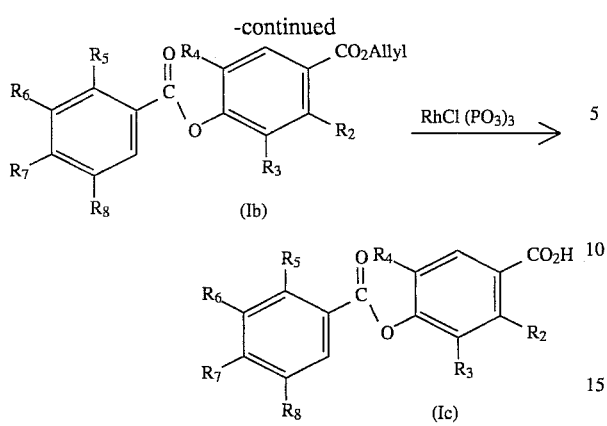

The action of the acid chloride (1) with an allyl p-hydroxybenzoate (2), optionally mono- or polysubstituted, in the presence of a tertiary amine such as pyridine or triethylamine, leads to allylic esters (Ib). The synthesis route to the free acid can be carried out by means of a catalyst such as certain complexes of a transition metal such as tris (triphenylphosphine) rhodium (1) chloride or tetrakis (triphenylphosphine) palladium (O) in the presence of a secondary amine.

The acid (Ic) thus obtained can be converted in a known manner into the corresponding acid chloride which, when treated

gives the corresponding ester or amide.

The present invention also relates to, as a medicine, the compounds of formula (I) such as defined above.

The compounds in accordance with the present invention exhibit good stability to light and oxygen.

These compounds exhibit good activity in the differentiation test of mice embryonic teratocarcinoma cells (F9 cells) (Cancer Research 43, p. 5268, 1983), and/or in the inhibition test of ornithine decarboxylase after induction by "tape stripping" nude rat (Lab. Animale 21, p. 233–240, 1987) and/or in the ear edema test induced by topical application of arachidonic acid on mice (J. Invest. Dermatol. 82, p. 367–371, 1984). These tests show the activities of the compounds respectively in the fields of differentiation, proliferation and inflammation.

Finally, the new compounds are characterized by the introduction, into the chemical structure, of an ester linkage highly sensitive to the action of various esterases in vivo, which lends to the rapid inactivation of the molecules by conversion into biologically inactive fragments.

The compounds in accordance with the present invention are indeed particularly suitable in the following treatment fields:

(1) for the treatment of dermatologic ailments linked to a keratinization disorder causing differentiation and proliferation and principally for treating common acne, comedons, polymorphs, nodulokystic acne, conglobata, senile acne, secondary acne such as solar, medicinal and professional acne;

(2) for the treatment of other types of keratinization disorders, principally ichthyoses, ichthyosiform conditions, Darier malady, palmoplantary keratodermies, leucophasies and leucoplasiform conditions and lichen;

(3) for the treatment of dermatologic ailments linked to a keratinization disorder having an inflammatory and/or immunoallergic component and principally, all forms of psoriasis, be they cutaneous, mucous or ungual, and even psoriasic rheumatism, or again cutaneous atopies, such as eczema, or respiratory atopy; the compounds can also be used in certain inflammatory ailments not exhibiting any keratinization disorder;

(4) for the treatment of all dermic or epidermic proliferations that are benign or malignant, that are either of viral origin such as common warts, plane warts and epidermodysplasie verruciform, the proliferation being able to be induced by ultraviolet radiations, principally in the case of baso epithelioma and cellular spino;

(5) for the treatment of other dermatologic disorders such as blistery dermatoses and collagen maladies;

(6) for the treatment of ophthalmologic disorders, and principally for the treatment of corneopathies;

(7) for combatting against ageing of the skin, be it photoinduced or not; and (8) to prevent or heal scars of epidermic and/or dermic atopies, induced by local or systemic corticosteroids, or any other form of cutaneous atophy.

The present invention also relates to medicinal compositions containing at least one compound of formula (I), such as defined above, or one of its salts.

The present invention thus relates to a new medicinal composition, intended principally for the treatment of the ailments mentioned above, comprising in a pharmaceutically acceptable support at least one compound of formula (I) and/or one of its salts.

The compounds according to the present invention are generally administered to a human or animal host at a daily dosage of about 0.01 mg/kg to 100 mg/kg of body weight.

As the vehicle or support for these compositions any conventional vehicle can be employed, the active component being found either in the dissolved state, or in the dispersed state, in said vehicle.

The administration of the compounds of the present invention can be effected enterally, parenterally, topically or ocularly.

When administered enterally the medicines can be provided in the form of tablets, gelules, lozenges, syrups, suspensions, solutions, powders, granules, emulsions or nanoparticles.

When administered parenterally, the medicinal compositions can be provided in the form of solutions, suspensions or nanoparticles for perfusion or injection.

When administered topically the pharmaceutical compositions based on the compounds in accordance with the present invention and intended for the treatment of the skin and mucous membranes are provided in the form of ointments, creams, milks, salves, powders, impregnated tampons, solutions, gels, lotions, sprays or suspensions. They can also be provided in the form of lipidic or polymeric microspheres or vesicles or polymeric patches or hydrogels so as to permit controlled release.

These topically applied compositions can be provided in anhydrous form or in aqueous form, according to clinical indications.

When administered ocularly, the medicinal composition is principally in the form of an eyewash.

These compositions contain at least one compound of formula (I) such as defined above or one of its salts, in an amount ranging, preferably, from 0.0001 to 5 percent by weight relative to the total weight of the composition.

The compounds of formula (I), in accordance with the present invention, are also useful in the cosmetic field, and in particular in body and hair hygiene compositions and principally for the treatment of skin having acne tendencies, to improve hair growth, to combat hair loss, to combat against an oily appearance of the skin or hair, for the protection against the harmful effects of the sun or in the treatment of physiologically dry skin.

The present invention thus relates to a cosmetic composition containing, in a cosmetically acceptable vehicle, an effective amount of at least one compound of formula I or one of its salts, this composition being provided principally in the form of a lotion, gel, soap or shampoo.

The concentration of the compound of formula I in these cosmetic compositions is between 0.0001 and 0.1 percent by weight and preferably between 0.001 and 0.01 percent by weight, based on the total weight of the composition.

The medicinal and cosmetic compositions according to the present invention can contain inert or even pharmacodynamic or cosmetically active additives and principally: hydrating agents such as thiamorpholinone and its derivatives or urea; antiseborrheic or anti-acne agents such as S-carboxymethyl- cysteine, S-benzycysteamine, their salts and their derivatives, tioxolane or benzoyl peroxide; antibiotics such as erythromycin and its esters, neomycin, tetracycline or 4,5-polymethylene-3-isothiazolinones; agents promoting the growth of hair, such as "Minoxidil" (2,4-diamino-6-piperidino-3-pyrimidine oxide) and its derivatives, Diazoxide (7-chloro-3-methyl-l,2,4 -benzothiadiazino-1,1-dioxide) and Phenytoin (5,5-diphenyl-2,4-imidazolidine dione); steroidal and non-steroidal anti-inflammatory agents; carotenoids and, principally, β-carotene; anti-psoriasic agents such as anthralin and its derivatives and 5,8,11,4-eicosatetraynoic and 5,8,11-eicosatriynoic acids, and their esters and amides.

The compositions according to the present invention can also include flavor improving agents, preservatives, stabilizers, humidity regulating agents, pH regulating agents, osmotic pressure modifying agents, emulsifiers, UV-A and UV-B filters, and antioxidants such as α-tocopherol, butylhydroxyanisole or butylhydroxytoluene.

The following non-limiting examples illustrate the preparation of the active compounds of formula I according to the present invention as well as compositions containing these compounds.

EXAMPLES OF PREPARATION

Example 1

4-[3-(1-adamantyl)-4-methoxybenzoyloxy-] 3-fluorobenzoic acid (a) allyl 3-fluoro-4-hydroxybenzoate Into a round bottom flask, there are introduced 5.35 g (35 mmoles) of 3-fluoro-4-hydroxybenzoic acid and 50 ml of allyl alcohol. 1.5 ml of concentrated sulfuric acid are added and the mixture is heated to 100° C. for 12 hours. The reaction medium is evaporated to dryness and 200 ml of water are added. The reaction medium is neutralized with sodium bicarbonate and extracted with dichloromethane. The organic phase is decanted, washed with water, dried on magnesium sulfate and evaporated. The residue obtained is purified by chromatography on a silica column by eluting with an 80:20 mixture of dichloromethane and hexane. 3.7 g (55% yield) of the expected ester having a melting point of 42°–43° C. are recovered.

(b) allyl 4-(1-adamantyl)-4-methoxy benzoyloxy-] 3-fluorobenzoate

The 3-(1-adamantyl)-4-methoxybenzoyl chloride prepared starting with 2.8 (10 mmoles) of 3-(1-adamantyl)-4-methoxy benzoic acid, described in Example 1(b) of European patent application No. 0.232.199 is dissolved in 50 ml of tetrahydrofuran (THF). The solution is slowly added to a mixture of 1.96 g (10 mmoles) of allyl 3-fluoro-4-hydroxybenzoate and 1.5 ml (10 mmoles) of triethylamine in 50 ml of THF. The mixture is stirred for 12 hours at ambient temperature. The reaction medium is then poured into water, and extracted with ethyl ether. The organic phase is decanted, washed with water, dried on magnesium sulfate and evaporated. The residue is purified by chromatography on a silica column by eluting with a 50:50 mixture of dichloromethane and hexane. After evaporation of the solvents, 3.3 g (72% yield) of the expected ester having a melting point of 123°–125° C. are obtained.

(c) 4-[3-(1-adamantyl)-4-methoxybenzoyloxy]-3 -fluorobenzoic acid

Into a round bottom flask and under a nitrogen stream, there are introduced 108 mg (3.6 mmoles) of sodium hydride (80% in oil) and 20 ml of THF). There are then slowly added 546 μl (3.6 mmoles) of ethyl malonate and the mixture is stirred at ambient temperature until the cessation of gaseous emission.

This solution is slowly introduced into a mixture of 1.65 g (3.6 mmoles) of the ester obtained in Example 1(b) above, 208 mg of tetrakis (triphenylphosphine palladium (O) and 30 ml of THF. The reaction mixture is stirred for 1 hour at ambient temperature, and then evaporated. The resulting residue is pulverized in 100 ml of ethyl ether and the sodium salt is filtered. The solid is introduced into 100 ml of water, acidified to pH 1 with concentrated HCl and extracted with ethyl ether. The organic phase is decanted, dried on magnesium sulfate and evaporated. 1.1 g (72% yield) of 4-[3-(1-adamantyl)-4-methoxybenzoyloxy]-3-fluorobenzoic acid having a melting point of 258°–260° C. are obtained.

Example 2

4-[3-(1-adamantyl)-4-methoxybenzoyloxy-] 2-fluorobenzoic acid (a) allyl 2-fluoro-4-hydroxybenzoate In a manner analogous to Example 1(a), starting with 8.3 g (53 mmoles) of 2-fluoro-4-hydroxybenzoic acid treated for 2 hours at 100° C. with 60 ml of allyl alcohol and 1.5 ml of concentrated sulfuric acid, 7.2 g (69% yield) of the expected ester having a melting point of 80°–81° C. are obtained.

(b) allyl 4-[3-(1-adamantyl)-4-methoxybenzoyloxy-] 2-fluorobenzoate

To a mixture of 1.96 g (10 mmoles) of allyl 2-fluoro-4-hydroxybenzoate, 1.53 ml (11 mmoles) of triethylamine and 25 ml of THF, there is slowly added a solution of 3 g (10 mmoles) of 3 -(1-adamantyl)-4-methoxybenzoyl chloride in 50 ml of THF. The reaction medium is stirred at ambient temperature for 12 hours and then poured into water and extracted with ethyl ether. The organic phase is decanted, washed with water, dried on magnesium sulfate and evaporated. The resulting residue is purified by chromatography on a silica column, eluted by a 50:50 mixture of dichloromethane and hexane. After evaporation of the solvents, 3.63 g (78% yield) of the expected ester having a melting point of 102°–104° C. are obtained.

(c) 4-[3-(1-adamantyl)-4-methoxybenzoyloxy-] 2-fluorobenzoic acid

Into a three neck flask and under a nitrogen current, there are introduced 2.32 g (5 mmoles) of the ester obtained in 2(b), above, 145 mg of tetrakis (triphenylphosphine) palladium (O) and 25 ml of anhydrous THF. There are then slowly added 4.35 ml (50 mmoles of morpholine and the mixture is stirred at ambient temperature for 1 hour. The reaction medium is evaporated to dryness and the residue is pulverized in ethyl ether. The formed morpholine salt is filtered off and introduced into 100 ml of water, acidified to pH 1 with concentrated HCl and extracted with ethyl ether. The organic phase is decanted, washed with water, dried on magnesium sulfate and evaporated. The solid is pulverized in 20 ml of ethyl ether, filtered and dried. 1.86 g (88% yield) of the expected acid having a melting point of 254°–256° C. are obtained.

Example 3

4-[3-(1-adamantyl)-4-methoxybenzoyloxy-] 2-methylbenzoic acid (a) allyl 4-hydroxy-2-methylbenzoate In a manner analogous to Example 1(a), 5.34 g (32 mmoles) of 4-hydroxy-2-methyl benzoic acid treated at 100° C. for 12 hours with 50 ml of allyl alcohol and 1.5 ml of concentrated sulfuric acid, give 4 g (76% yield) of the expected ester having a melting point of 76°–77° C.

(b) allyl 4-[3-(1-adamantyl)-4-methoxybenzoyloxy-] 2-methylbenzoate

Into a three neck flask and under a nitrogen current, there are introduced 330 mg (11 mmoles) of sodium hydride (80% in oil) and 20 ml of THF. There is then slowly added a solution of 1.92 g (10 mmoles) of the ester prepared in Example 3(a), above, and the mixture is stirred at ambient temperature until the cessation of gaseous emission. There is then slowly introduced a solution of 3 g (10 mmoles) of 3-(1-adamantyl)-4-methoxybenzoyl chloride in 30 ml of THF and the mixture is stirred at ambient temperature for six hours. The reaction medium is poured into water and extracted with ethyl ether. The organic phase is decanted, washed with water, dried on magnesium sulfate and evaporated. The resulting residue is purified by chromatography on a silica column, eluted with a 40:60 mixture of dichloromethane and hexane. After evaporation of the solvents, 2.9 g (63% yield) of the expected ester having a melting point of 136°–137° C. are recovered.

(c) 4-[3-(1-adamantyl)-4-methoxybenzoyloxy-2 -methylbenzoic acid

In a manner analogous to Example 2(c), starting with 1.38 g (3 mmoles) of allyl 4-[3-(1-adamantyl)-4-methoxybenzoyloxy]-2-methylbenzoate, 780 mg of 4-[3-(1-adamantyl)-4-methoxybenzoyloxy]-2-methylbenzoic acid having a melting point of 236°–237° C. are obtained.

Example 4

4-[3-(1-adamantyl)-4-methoxybenzoyloxy-] 2-hydroxybenzoic acid (a) benzyl 2,4-dihydroxybenzoate To a solution of 3 g (0.1 mole) of sodium hydride (80% in oil) and 50 ml of dimethylformamide (DMF), there are slowly added 15.4 g (0.1 mole) of 2,4-dihydroxybenzoic acid dissolved in 50 ml of DMF. The mixture is stirred at ambient temperature until the cessation of gaseous emission.

There are then added 13.1 ml (0.1 mole) of benzyl bromide and the mixture is stirred at ambient temperature until solubilization of the reaction medium. The reaction mixture is poured into water, and extracted with ethyl ether. The organic phase is decanted, washed with water, dried on magnesium sulfate and evaporated. The residue is purified by chromatography on a silica column by eluting with dichloromethane. 19.7 g (81% yield) of the expected ester having a melting point of 94°–95° C. are recovered.

(b) benzyl 4-[3-(1-adamantyl)-4-methoxybenzoyloxy-] 2-hydroxybenzoate

In a manner analogous to Example 2(b) starting with 9.8 g (40 mmoles) of benzyl 2,4-dihydroxybenzoate, 16.5 g (81% yield) of benzyl 4-[3-(1-adamantyl)-4-methoxybenzoyloxy]-2-hydroxybenzoate having a melting point of 171°–172° C. are obtained.

(c) 4-[3-(1-adamantyl)-4-methoxybenzoyloxy-] 2-hydroxybenzoic acid

Into a reactor, there are introduced 5.1 g (10 mmoles) of the ester obtained in Example 4(b) above, 1 g of palladium on charcoal (5%) and 250 ml of dioxan. Hydrogenation is carried out at ambient temperature and under a pressure of 4 bars, for 1 hour. The catalyst is filtered and the filtrate is evaporated. The resulting solid is pulverized in 100 ml of ethyl ether. After filtering and drying, 3.6 g (86% yield) of 4-[3-(1-adamantyl)-4-methoxybenzoyloxy]-2-hydroxy benzoic acid having a melting point of 243°–244° C. are obtained.

Example 5

4-[3-(1-adamantyl)-4-methoxybenzoyloxy-] 2-methoxybenzoic acid (a) benzyl 4-[3-(1-adamantyl)-4-methoxybenzoyloxy-] 2-methoxybenzoate To a solution of 5.12 g (10 mmoles) of benzoyl 4-[3-(1-adamantyl)-4-methoxybenzoyloxy]-2-hydroxybenzoate and 200 ml of DMF, there are added, in small portions, 360 mg (12 mmoles) of sodium hydride (80% in oil). The mixture is stirred at ambient temperature until the cessation of gaseous emission. 750 μl (12 mmoles) of methyl iodide are added and the mixture is stirred for 4 hours at ambient temperature. The reaction medium is poured into water and extracted with 300 ml of ethyl ether. The organic phase is decanted, washed with water, dried on magnesium sulfate and evaporated. The resulting residue is purified by chromatography on a silica column eluted with dichloromethane. After evaporation of the solvent, 4.9 g (94% yield) of the expected ester having a melting point of 102°–103° C. are recovered.

(b) 4-[3-(1-adamantyl)-4-methoxybenzoyloxy]-2 -methoxybenzoic acid

Into a reactor, there are introduced 4.5 g (8.5 mmoles) of the benzylic ester obtained in Example 5(a), above, 450 mg of palladium on charcoal (5%) and 120 ml of dioxan. Hydrogenation is effected at ambient temperature and under a pressure of 4 bars for 2 hours. The catalyst is filtered and the filtrate is evaporated. The resulting solid is pulverized in 50 ml of ethyl ether, filtered and dried. 3 g (82% yield) of 4-[3-(1-admamantyl)-4-methoxybenzoyloxy]-2-methoxybenzoic acid having a melting point of 199°–200° C. are recovered.

Example 6

4-[3-(1-adamantyl)-4-methoxybenzoyloxy]-3 -methoxybenzoic acid (a) allyl 4-hydroxy-3-methoxybenzoate In a manner analogous to Example 1(a), 5 g (30 mmoles)

of 4-hydroxy-3-methoxybenzoic acid treated at 100° C. for 4 hours with 50 ml of allyl alcohol and 820 µl of concentrated sulfuric acid, give 4.65 g (75% yield) of the expected ester in the form of a slightly yellow oil.

(b) allyl 4-[3-(1-adamantyl)-4-methoxybenzoyloxy-] 3-methoxybenzoate

In a manner analogous to Example 2(b) starting with 2.35 g (12 mmoles) of allyl 4-hydroxy-3-methoxy benzoate, 4.12 g (77% yield) of the expected ester having a melting point of 146°–148° C. are obtained.

(c) 4-[3-(1-adamantyl)-4-methoxybenzoyloxy-] 3-methoxybenzoic acid

In a manner analogous to Example 1(c), starting with 2 g (4.2 mmoles) of the ester prepared in Example 6(b), 1.35 g (74% yield) of 4-[3-(1-adamantyl)-4-methoxybenzoyloxy]-3-methoxybenzoic acid having a melting point of 282°–284° C. are obtained.

Example 7

4-[3-(1-adamantyl)-4-methoxybenzoyloxy-] 2-trifluoromethylbenzoic acid (a) allyl 4-hydroxy-2-trifluoromethylbenzoate In a manner analogous to Example 1(a) starting with 2 g (9.7 mmoles) of 4-hydroxy-2-trifluoromethylbenzoic acid treated at 100° C. for 12 hours with 20 ml of allyl alcohol and 260 µl of concentrated sulfuric acid, give 1.4 g (59% yield) of the expected ester having a melting point of 82°–83°.

(b) allyl 4-[3-(1-adamantyl)-4-methoxybenzoyloxy-] 2-trifluoromethylbenzoate

In a manner analogous to Example 2(b) 1.78 g (66% yield) of the expected ester having a melting point of 100°–102° C. are obtained.

(c) 4-[3-(1-adamantyl)-4-methoxybenzoyloxy-] 2-trifluoromethylbenzoic acid

In a manner analogous to Example 1(c), starting with 1.78 g (3.46 mmoles) of the allyl ester prepared in Example 7(b) above, 700 mg° (39% yield) of the expected acid having a melting point of 228°–230° C. are obtained.

Example 8

Methyl 4-[3-(1-adamantyl)-4-methoxybenzoyloxy-] 2-hydroxybenzoate

Into a round bottom flask, there are introduced 1.68 g (10 mmoles) of methyl 2,4-dihydroxybenzoate, 1.55 ml (11 moles) of triethylamine and 50 ml of THF. There is then slowly added a solution of 3 g (10 mmoles) of 3-(1-adamantyl)-4-methoxybenzoyl chloride in 50 ml of THF and the mixture is stirred at ambient temperature for 12 hours. The reaction medium is poured into water and extracted with ethyl ether. The organic phase is decanted, washed with water, dried on magnesium sulfate and evaporated. The resulting residue is purified by chromatography on a silica column eluted by a 50:50 mixture of dichloromethane and hexane. After evaporation of the solvents, 2.55 g (59% yield) of methyl 4-[3-(1-adamantyl)-4-methoxybenzoyloxy]-2-hydroxybenzoate having a melting point of 125°–127° C. are recovered.

Example 9

4-[5-(1-adamantyl)-2-fluoro-4-methoxybenzoyloxy] benzoic acid (a) allyl 5-(1-adamantyl)-2-fluoro-4-hydroxy benzoate To a solution of 3 g (20 mmoles) of 1-adamantanol in 10 ml of n-heptane, there are added, successively, 63 µl of concentrated sulfuric acid and 2.16 ml (23 mmoles) of acetic anhydride. The mixture is stirred at ambient temperature for 3 hours. There are then slowly added 540 µl (10 mmoles) of concentrated sulfuric acid and then a solution of 3.92 g (20 mmoles) of allyl 2-fluoro-4-hydroxybenzoate in 50 ml of dichloromethane. This mixture is stirred for 24 hours at ambient temperature. The reaction medium is evporated to dryness and the residue is introduced into water and neutralized with sodium bicarbonate. The resulting solid is filtered and dried. The solid is purified by chromatography on a silica column by eluting with dichloromethane. After evaporation of the solvents, 3.86 g (58% yield) of the expected ester having a melting point of 219°–222° C. are recovered.

(b) allyl 5-(1-adamantyl)-2-fluoro-4-methoxy benzoate

Into a three neck flask and under a nitrogen current, there are introduced 350 mg (11.6 mmoles) of sodium hydride (80% in oil) and 10 ml of DMF. There is then slowly added a solution of 3.84 g (11.6 mmoles) of the ester prepared in Example 9(a), above, in 30 ml of DMF. The mixture is stirred at ambient temperature until the cessation of gaseous emission. 730 µl (11.7 mmoles) of methyl iodide are slowly added and the mixture is stirred at ambient temperature for 6 hours. The reaction medium is poured into water and extracted with ethyl ether. The organic phase is decanted, washed with water, dried on magnesium sulfate and evaporated. The resulting residue is purified by chromatography on a silica column eluted with a 50:50 mixture of dichloromethane and hexane. After evaporation of the solvents, 2.9 g (72% yield) of allyl 5-(1-adamantyl)-2-fluoro-4-methoxybenzoate having a melting point of 101°–102° C. are recovered.

(c) 5-(1-adamantyl)-2-fluoro-4-methoxybenzoic acid

A suspension of 2.87 g (8.3 mmoles) of the ester obtained in Example 9(b), above, in 100 ml of 2N methanolic soda is heated at reflux for 6 hours. It is then evporated to dryness and the residue is taken up in water, acidified to pH 1 with concentrated HCl and extracted with ethyl ether. The organic phase is decanted, washed with water, dried on magnesium sulfate and evaporated. 2.5 g (100% yield) of the expected acid which melts at 282°–284° C. are obtained.

(d) 5-(1-adamantyl)-2-fluoro-4-methoxybenzoyl chloride 2.13 g (7 mmoles) of 5-(1-adamantyl)-2-fluoro-4-methoxybenzoic acid and 20 ml of thionyl chloride are heated at reflux until the cessation of gaseous emission. It is then evaporated to dryness and 2.26 g (100% yield) of the crude acid chloride, which is used as such for the following synthesis, are obtained.

(e) allyl 4-[5-(1-adamantyl)-2-fluoro-4-methoxybenzoyloxy]benzoate

Into a round bottom flask there are introduced 1.25 g (7 mmoles) of allyl 4-hydroxybenzoate, 1.1 ml (7 mmoles) of triethylamine and 20 ml of THF. There is slowly added a solution of 2.26 g (7 mmoles) of the acid chloride prepared in Example 9(d) in 60 ml of THF. The mixture is stirred at ambient temperature for 20 hours. The reaction medium is poured into water, and extracted with ethyl ether. The organic phase is decanted, washed with water, dried on magnesium sulfate and evaporated. The resulting residue is Purified by chromatography on a silica column by eluting with 70:30 mixture of dichloromethane and hexane. After evaporation of the solvents, 2.4 g (74% yield) of the expected ester having a melting point of 130°–131° C. are recovered.

(f) 4-[5-(1-adamantyl)-2-fluoro-4-methoxybenzoyloxy]benzoic acid

In a manner analogous to Example 1(c), starting with 2.33 g (5 mmoles) of allyl 4-[5-(1-adamantyl)-2-fluoro-4-methoxybenzoyloxy]benzoate, 1.69 g (79% yield) of 4-[5-(1-adamantyl)-2-fluoro-4-methoxybenzoyloxy]benzoic acid having a melting point of 268°–270° C. are obtained.

Example 10

4-[5-(1-adamantyl)-2,4-dimethoxybenzoyloxy]benzoic acid (a) methyl 5-(1-adamantyl)-2,4-dihydroxybenzoate In a manner analogous to Example 9(a), starting with 24.5 g (0.146 mole) of methyl 2,4-dihydroxybenzoate, 32.5 g (74% yield) of methyl 5-(1-adamantyl)-2,4-dihydroxybenzoate having a melting point of 167°–169° C. are obtained.

(b) methyl 5-(1-adamantyl)-2,4-dimethoxybenzoate

To a suspension of 1.32 g (44 mmoles) of sodium hydride (80% in oil) in 30 ml of DMF, there is slowly added a solution of 6 g (20 mmoles) of the ester prepared in Example 10(a) above in 100 ml of DMF. The mixture is stirred at ambient temperature until the cessation of gaseous emission. There are then added 2.75 ml (44 mmoles) of methyl iodide and the mixture is stirred at ambient temperature for 24 hours. The reaction medium is poured into water and extracted with ethyl ether. The organic phase is decanted, washed with water, dried on magnesium sulfate and evaporated. The resulting residue is purified by chromatography on a silica column eluted with a 90:10 mixture of dichloromethane and hexane. After evaporation of the solvents, 3.4 g (51% yield) of the expected ester having a melting point of 148°–151° C. are recovered.

(c) 5-(1-adamantyl)-2,4-dimethoxybenzoic acid

In a manner analogous to Example 9(c), starting with 3.3 g (10 mmoles) of the methyl ester prepared in Example 10(b) above, 3 g (94% yield) of 5-(1-adamantyl)-2,4-dimethoxybenzoic acid having a melting point of 213°–214° C. are obtained.

(d) 5-(1-adamantyl)-2,4-dimethoxybenzoyl chloride

In a manner analogous to Example 9(d), starting with 2.94 g (9.3 mmoles) of 5-(1-adamantyl)-2,4-dimethoxybenzoic acid, 3.12 g (100% yield) of the crude acid chloride, which is used as such in the following synthesis, are obtained.

(e) allyl 4-[5-(1-adamantyl)-2,4-dimethoxybenzoyloxy]benzoate

In a manner analogous to Example 9(e), by the reaction of 3.12 g (9.3 mmoles) of the acid chloride prepared in Example 10(d), above, with 1.66 g (9.3 mmoles) of allyl 4-hydroxybenzoate, 1.8 g (41% yield) of the expected ester having a melting point of 120°–121° C. are obtained.

(f) 4-[5-(1-adamantyl)-2,4-dimethoxybenzoyloxy]benzoic acid

In a manner analogous to Example 1(c), starting with 1.77 g (3.71 mmoles) of the ester prepared in Example 10(e), above, 1.16 g (72% yield) of 4-[5-(1-adamantyl)-2,4-dimethoxy-benzoyloxy]benzoic acid having a melting point of 236°–238° C. are obtained.

Example 11

4-[3-(1-adamantyl)benzoyloxy]benzoic acid (a) methyl 3-(1-adamantyl)-4-hydroxybenzoate In a manner analogous to Example 9(a), starting with 22.8 g (0.15 mole) of methyl 4-hydroxybenzoate, 36 g (84% yield) of methyl 3-(1-adamantyl)-4-hydroxybenzoate having a melting point of 183°–184° C. are obtained.

(b) methyl 3-(1-adamantyl)-4-(trifluoromethyl) sulfonyloxy benzoate

A solution of 14.4 g (50.4 mmoles) of methyl 3-(1-adamantyl)-4-hydroxybenzoate, 13.6 ml (168 mmoles) of pyridine, 61 mg (0.5 mmoles) of 4-dimethylaminopyridine and 100 ml of anhydrous dichloromethane sulfonic anhydride is cooled to −78° C. There are slowly added 10 ml (59.5 mmoles) of trifluoromethane. The temperature is permitted to rise to 20° C. and the mixture is stirred for 6 hours. The reaction medium is poured into water, acidified to pH 1 with concentrated HCl and extracted with dichloromethane. The organic phase is decanted, washed with water, dried on magnesium sulfate and evaporated. The resulting residue is purified by chromatography on a silica column by eluting with hexane. After evaporation of the solvents, 17.5 g (83% yield) of the expected product having a melting point of 90°–91° C. are obtained.

(c) methyl 3-(1-adamantyl)benzoate

Into a round bottom flask, there are introduced 3 g (7 mmoles) of methyl 3-(1-adamantyl)-4-(trifluoromethyl) sulfonyloxybenzoate, 415 mg (0.36 mmoles) of tetrakis (triphenylphosphine) palladium (O), 3 ml (21.5 mmoles) of triethylamine and 15 ml of DMF. There are then slowly added 547 µl (14.4 mmoles) of formic acid and the mixture is heated at 80° C. for 1 hour. The reaction medium is poured into water and extracted with ethyl ether. The organic phase decanted, washed with water, dried on magnesium sulfate and evaporated. The resulting residue is purified by chromatography on a silica column eluted with hexane. 1.78 g (90% yield) of methyl 3-(1adamantyl)benzoate having a melting point of 147°–149° C. are recovered.

(d) 3-(1-adamantyl)benzoic acid

In a manner analogous to Example 9(c), starting with 3.45 g (12.7 mmoles) of the ester prepared in Example 11(c), 2.81 g (86% yield) of 3-(1-adamantyl)benzoic acid having a melting point of 247°–249° C. are obtained.

(e) 3-(1-adamantyl)benzoyl chloride

In a manner analogous to Example 9(d) starting with 1.4 g (5.5 mmoles) of 3-(1-adamantyl)benzoic acid, 1.5 g (100% yield) of the crude acid chloride, which is used as such in the following synthesis, are obtained.

(f) allyl 4-[3-(1-adamantyl)benzoyloxy]benzoate

In a manner analogous to Example 9(a) by reacting 1.5 g (5.5 mmoles) of 3-(1-adamantyl)benzoyl chloride with 980 mg (5.5 mmoles) of allyl 4-hydroxybenzoate, 1.5 g (68% yield) of the expected ester in the form of a colorless oil are obtained.

(g) 4-[3-(1-adamantyl)benzoyloxy]benzoic acid

In a manner analogous to Example 1(c), starting with 1.45 g (3.6 mmoles) of allyl 4-[3-(1-adamantyl)benzoyloxy]benzoate, 600 mg (40% yield) of 4-[3-(1-adamantyl)benzoyloxy]benzoic acid having a melting point of 237°–239° C. are obtained.

Example 12

4-[3,5-di-tert.butyl-4-hydroxybenzoyloxy]benzoic acid (a) 3,5-di-tert.butyl-4-hydroxybenzoyl chloride 1.88 g (7.5 mmoles) of 3,5-di-tert.butyl-4-hydroxybenzoic acid and 15 ml of thionyl chloride are heated at reflux until the cessation of gaseous emission. It is then evaporated to dryness and 2.1 g (100% yield) of the crude acid chloride, which is used as such in the following synthesis, are obtained.

(b) allyl 4-(3,5-di-tert.butyl-4-hydroxybenzoyloxy]benzoate

In a manner analogous to Example 9(c), starting with 2.1 g (7.5 mmoles) of the acid chloride prepared in Example 12(a) above with 1 g (7.5 mmoles) of allyl 4-hydroxybenzoate, 1.48 g (49% yield) of the expected ester having a melting point of 114°–116° C. are obtained.

(c) 4-[3,5-di-tert.butyl-4-hydroxybenzoyloxy]benzoic acid

In a manner analogous to Example 2(c), starting with 1.47 g (3.6 mmoles) of the ester prepared in Example 12(b), 750 mg (57% yield) of 4-(3,5-di-tert.butyl-4-hydroxybenzoyloxy]benzoic acid which melts at 223°–224° C. are obtained.

Example 13

4-[3-(1-adamantyl)-4-vinylbenzoyloxy]benzoic acid

In a round bottom flask under argon, there are introduced 4.1 g (10 mmoles) of methyl 3-(1-adamantyl)-4-(trifluoromethyl) sulfonyloxybenzoate in 50 ml of DMF. There are then added, successively, 3.1 ml of vinyltributyltin (10.3 mmoles), 1..3 g (30 mmoles) of lithium chloride and 141 mg (0.2 mmoles) of bis(triphenylphosphine) palladium (II) chloride. The mixture is heated at 80° C. for 16 hours. The reaction medium is poured into water, and extracted with ethyl ether. The organic phase is decanted, dried on magnesium sulfate and evaporated. The resulting residue is purified by chromatography on a silica column eluted by a 20:80 mixture of dichloromethane and hexane. 2.7 g (93% yield) of the expected product having a melting point of 86°–87° C. are recovered.

(b) 3-(1-adamantyl)-4-vinylbenzoic acid

Into a round bottom flask there are introduced 1.48 g (5 mmoles) of the preceding ester, 100 ml of 2N methanolic soda and 250 ml of THF. The mixture is stirred at ambient temperature for 3 hours, and then evaporated to dryness. The resulting residue is taken up in water and acidified to pH 1 with concentrated HCl. The resulting solid is filtered and dried under a vacuum in the presence of phosphorus pentoxide. 1.4 g (100% yield) of the expected product having a melting point of 315°–317° C. are recovered.

(c) 3-(1-adamantyl)-4-vinylbenzoyl chloride

Into a round bottom flask, there are introduced 1.4 g (5 mmoles) of 3-(1-adamantyl)-4-vinylbenzoic acid in 100 ml of dichloromethane. There are slowly added 940 µl (5 mmoles) of dicyclohexylamine. After obtaining a homogenous reaction medium, there are slowly added 360 µl (5 mmoles) of thionyl chloride and the mixture is stirred at ambient temperature for 1 hour. It is then evaporated to dryness and the residue is taken up in 200 ml of ethyl ether. The dicyclohexylamine salt is filtered and the filtrate is evaporated. 1.5 g (100% yield) of the crude acid chloride, which is used as such for the following synthesis, are obtained.

(d) allyl 4-[3-(1-adamantyl)-4-vinylbenzoyloxy]benzoate

In a manner analogous to Example 9(e) by reacting 1.35 g (4.5 mmoles) of 3-(1-adamantyl)-4-vinylbenzoyl chloride with 800 mg (4.5 mmoles) of allyl 4-hydroxybenzoate, 1.4 g (70% yield) of the expected ester in the form of a colorless oil are obtained.

(e) 4-[3-(1-adamantyl)-4-vinylbenzoyloxy]benzoic acid In a manner analogous to Example 2(c), starting with 1.2 g (2.7 mmoles) of allyl 4-[3-(1-adamantyl)-4-vinylbenzoyloxy]benzoate, 750 mg (75% yield) of 4-[3-(1-adamantyl)-4vinylbenzoyloxy]benzoic acid having a melting point of 235°–236° C. are obtained.

Example 14

4-[3-(1-adamantyl)-4-ethylbenzoyloxy]benzoic acid (a) methyl 3-(1-adamantyl)-4-ethylbenzoate Into a reactor there are introduced 3 g (10 mmoles) of methyl 3-(1-adamantyl)-4-vinylbenzoate, 270 mg of palladium on charcoal (5%) and 50 ml of dioxan. Hydrogenation is effected at ambient temperature and under a pressure of 4 bars for 4 hours. The catalyst is filtered and the filtrate is evaporated. 3 g (100% yield) of the expected product in the form of a colorless oil are recovered.

(b) 3-(1-adamantyl)-4-ethylbenzoic acid

In a manner analogous to Example 13(b) starting with 2.54 g (8.5 mmoles) of the preceding ester. 2.4 g (100% yield) of 3 -(1-adamantyl)-4-ethylbenzoic acid are obtained.

(c) 3-(1-adamantyl)-4-ethylbenzoyl chloride

In a manner analogous to Example 9(d), starting with 2.3 g (8.1 mmoles) of the preceding acid, 2.35 g (100% yield) of the crude acid chloride, which is used as such in the following synthesis, are obtained.

(d) allyl 4-[3-(1-adamantyl)-4-ethylbenzoyloxy]benzoate

In a manner analogous to Example 9(e), by reacting 2.35 g (8.1 mmoles) of 3-(1-adamantyl)-4-ethylbenzoyl chloride with 1.44 g (8.1 mmoles) of allyl 4-hydroxybenzoate, 2.54 g (71% yield) of the expected ester having a melting point of 111°–113° C. are obtained.

(e) 4-[3-(1-adamantyl)-4-ethylbenzoyloxy]benzoic acid

In a manner analogous to Example 2(c), starting with 2.5 g (5.6 mmoles) of the ester prepared in Example 14(d), above, 1.65 g (73% yield) of 4-[3-(1-adamantyl)-4-ethylbenzoyloxy]benzoic acid having a melting point of 239°–241° C. are obtained.

Example 15

4-[3-(1-adamantyl)-4-butylbenzoyloxy]benzoic acid

Into a round bottom flask and under argon, there are introduced 4.1 g (10 mmoles) of methyl 3-(1-adamantyl)-4-(trifluoromethyl)sulfonyloxybenzoate in 50 ml of DMF. There are then added, successively, 3.6 ml (11 mmoles) of tetrabutyltin, 1.3 g (30 mmoles) of lithium chloride and 141 mg (0.2 mmole) of bis-(triphenylphosphine) palladium (II) chloride. The mixture is heated at 80° C. for 24 hours. The reaction medium is poured into water and extracted with ethyl ether. The organic phase is decanted, dried on magnesium sulfate and evaporated. The resulting residue is purified by chromatography on a silica column by eluting with a 30:70 mixture of dichloromethane and hexane. After evaporation of the solvents, 2.6 g (80% yield) of the expected product in the form of slightly yellow oil are obtained.

(b) 3-(1-adamantyl)-4-butylbenzoic acid

In a manner analogous to Example 13(b), starting with 2.3 g (7 mmoles) of the preceding ester, 2.1 g (100% yield) of 3-(1-adamantyl)-4-butylbenzoic acid having a melting point of 209°–210° C. are obtained.

(c) 3-(1-adamantyl)-4-butylbenzoyl chloride.

In a manner analogous to Example 9(d) starting with 2 g (6.4 mmoles) of the preceding acid, 2.1 g (100% yield) of the crude acid chloride, which is used as such in the following synthesis, are obtained.

(d) benzyl 4-[3-(1-adamantyl)-4-butylbenzoyloxy]benzoate

The preceding acid chloride dissolved in 50 ml of THF is slowly added to a mixture of 1.46 g (6.4 mmoles) of benzyl 4-hydroxybenzoate and 1 ml (7.1 mmoles) of triethylamine in 50 ml of THF. The mixture is stirred at ambient temperature for 8 hours. The reaction medium is poured into water and extracted with ethyl ether. The organic phase is decanted, dried on magnesium sulfate and evaporated. The resulting residue is purified by chromatography on a silica column by eluting with a 50:50 mixture of dichloromethane and hexane. After evaporation of the solvents, 2.2 g (75% yield) of the expected ester in the form of a colorless oil are recovered.

(e) 4-[3-(1-adamantyl)-4-butylbenzoyloxy]benzoic acid

Into a reactor, there are introduced 2 g (3.8 mmoles) of the ester prepared in Examples 15(d), 340 mg of palladium on charcoal (5%) and 100 ml of dioxan. Hydrogenation is effected at ambient temperature and under a pressure of 4 bars for 4 hours. The catalyst is filtered and the filtrate is evaporated. The resulting residue is purified by chromatography on a silica column eluted by a 70:30 mixture of dichloromethane and ethyl ether. After evaporation of the solvents, 1.1 g (68% yield) of 4-[3-(1-adamantyl)-4-butylbenzoyloxy]benzoic acid having a melting point of 205°–206° C. are recovered.

Example 16

4-[3-(1-adamantyl)-4-allyloxybenzoyloxy]benzoic acid

To a solution of 1.17 g (3 mmoles) of 4-[3-(1-adamantyl)-4-hydroxybenzoyloxy]benzoic acid in 100 ml of a 50:50 mixture of THF and DMF, there are added, by small portions, 180 mg (6 mmoles) of sodium hydride (80% in oil). The mixture is stirred at ambient temperature until the cessation of gaseous emission. There are then added 260 µl (3 mmoles) of allyl bromide and the mixture is stirred at ambient temperature for 3 hours. The reaction medium is poured into water, acidified to pH 4 with 1N HCl and extracted with ethyl ether. The organic phase, is decanted, washed with water, dried on magnesium sulfate and evaporated. The resulting residue is purified by chromatography on silica eluted with ethyl ether. After evaporation of the solvent, 880 mg (68% yield) of 4-[3-(1-adamantyl)-4-allyloxybenzoyloxy]benzoic acid having a melting point of 260°–261° C. are recovered.

Example 17

4-[3-(1-adamantyl)-4-methoxybenzoyloxy]isophthalic acid (a) benzyl 4-hydroxyisophthalate To a solution of 5.5 g (30 mmoles) of 4-hydroxyisophthalic acid in 200 ml of DMF, there are added, by small portions 1o8 g (60 mmoles) of sodium hydride (80% in oil). The mixture is stirred until the cessation of gaseous emission. There are then added 7.2 ml (60 mmoles) of benzil bromide and the mixture is stirred for 4 hours at ambient temperature. The reaction medium is poured into water and extracted with ethyl ether. The organic phase is decanted, washed with water, dried on magnesium sulfate and evaporated. The resulting residue is purified by chromatography on a silica column by eluting with a 30:70 mixture of dichloromethane and hexane. After evaporation of the solvents, 6.5 g (60% yield) of the expected ester having a melting point of 68°–70° C. are recovered.

(b) benzyl 4-[3-(1-adamantyl)-4-methoxybenzoyloxy]isophthalate

In a manner analogous to Example 1(b), by reacting 5.4 g (18 mmoles) of 3-(1-adamantyl)-4-methoxybenzyl chloride with 6.5 g (18 mmoles) of benzyl 4-hydroxyisophthalate, 7.5 g (67% yield) of benzyl 4-[3-(1-adamantyl)-4-methoxybenzoyloxy]isophthalate having a melting point of 102°–104° C. are obtained.

(c) 4-[3-(1-adamantyl)-4-methoxybenzoyloxy]isophthalic acid

In a manner analogous to Example 15(e), starting with 3.1 g (5 mmoles) of the preceding ester, 1.2 g (55% yield) of 4-[3-(1-adamantyl)-4-methoxybenzoyloxy]isophthalic acid having a melting point of 172°–173° C. are obtained.

Example 18

4-[3-(1-adamantyl)-4-methoxybenzoyloxy]benzenesulfonamide

Into a round bottom flask, there are introduced 2.86 g (10 mmoles) of 3-(1-adamantyl)-4-methoxybenzoic acid, 1.73 g (10 mmoles) of 4-hydroxybenzenesulfonamide and 50 ml of THF. There are added, successively, 2.1 g (10 mmoles) of 1,3-dicyclohexylcarbodiimide and then 1.22 (10 mmoles) of 4-dimethylaminopyridine. The medium is stirred at ambient temperature for 4 hours. The reaction medium is poured into water and extracted with ethyl ether. The organic phase is decanted, washed with water, dried on magnesium sulfate and evaporated. The resulting solid is purified by chromatography on a silica column eluted by a 60:40 mixture of ethyl ether and hexane. After evaporation of the solvents, 2 g (46% yield) of 4-[3-(1-adamantyl)-4-methoxybenzoyloxy]benzenesulfonamide having a melting point of 223°–224° C. are recovered.

Example 19

4-hydroxyphenyl 3-(1-adamantyl)-4-methoxybenzoate (a) 4-benzyloxyphenyl 3-(1-adamantyl)-4-methoxybenzoate Into a three neck flask, under a nitrogen current, containing 663 mg (22 mmoles) of sodium hydride (80% in oil), there are slowly added 4 g (20 mmoles) of 4-benzoyloxyphenol in 30 ml of anhydrous THF. The mixture is stirred until the cessation of gaseous emission. There are then slowly introduced 6.4 g (20 mmoles) of 3-(1-adamantyl)-4-methoxybenzoyl chloride in 60 ml of THF and the mixture is stirred at ambient temperature for 4 hours. The reaction medium is poured into water, extracted with dichloromethane, washed with water, dried on magnesium sulfate and evaporated. The resulting residue is pulverized in hexane yielding 9 g (96% yield) of the expected ester having a melting point of 183°–185° C.

(b) 4-hydroxyphenyl 3-(1-adamantyl)-4-methoxybenzoate

Into a reactor, there are introduced 4 g (8.5 mmoles) of the benzyl ether obtained in Example 19(a), 400 mg of palladium on charcoal (10%), 70 ml of dioxan, 70 ml of acetic acid and 0.2 ml of 12N HCl. The mixture is stirred at 50° C. under a pressure of 4 bars. After filtration and evaporation, the solid is taken up with 400 ml of dichloromethane and the organic phase is washed with water. After drying on magnesium sulfate, filtration and evaporation, 2.85 g (88% yield) of the expected product having a melting point of 236°–237° C. are isolated.

Example 20

Phenyl 3-(1-adamantyl)-4-methoxybenzoate

In a manner analogous to Example 3(b), 0.95 g (10 mmoles) of phenol in 10 ml of THF are treated with 332 mg (11 moles) of sodium hydride (80% in oil). There is then slowly introduced a solution of 3.2 g (10 mmoles) of 3-(1-adamantyl)-4-methoxybenzoyl chloride in 30 ml of THF. The reaction is permitted to proceed at ambient temperature for 4 hours. The reaction medium is poured into water, extracted with ethyl ether, washed with water, dried on magnesium sulfate and evaporated. The residue is chromatographed on silica, eluting with a 60:40 mixture of hexane and dichloromethane. After evaporation and precipitation in hexane, 3 g (83% yield) of the expected ester having a melting point of 165°–166° C. are isolated.

Example 21

4-methylphenyl 3-(1-adamantyl)-4-methoxybenzoate

In a manner analogous to Example 3(b), 1.08 g (10 mmoles) of paracresol in 10 ml of THF are treated with 332 mg (11 mmoles) of sodium hydride (80% in oil). There is then slowly introduced a solution of 3.2 g (10 mmoles) of 3-(1-adamantyl)-4-methoxybenzoyl chloride in 30 ml of THF. The reaction is permitted to proceed at ambient temperature overnight. The reaction medium is poured into water, extracted with ethyl acetate, washed with water, dried on magnesium sulfate and evaporated. The resulting residue is recrystallized in ethyl acetate yielding 2.91 g (77% yield) of 4-methylphenyl 3-(1-adamantyl)-4-methoxybenzoate having a melting point of 206° C.

Example 22

4-[3-(1-adamantyl)-4-methoxybenzoyloxy-] 3-hydroxymethylbenzoic acid (a) benzyl 4-hydroxy-3-hydroxymethylbenzoate A solution of 27.4 g (0.12 mole) of benzyl 4-hydroxybenzoate, 14.7 g (0.12 mole) of benzeneboronic acid, 6 g (0.135 mole) of paraformaldehyde and 0.9 ml (12 mmoles) of propionic acid in 600 ml of anhydrous benzene is heated at reflux for 12 hours using a Dean-Stark reactor to separate the water formed. The reaction medium is poured into bicarbonated water and extracted with ethyl ether. The organic phase is decanted, washed with water, dried on magnesium sulfate and evaporated. The resulting residue is purified by chromatography on a silica column eluted with dichloromethane. After evaporation of the solvent, 8.9 g (30% yield) of the expected product having a melting point of 109°–110° C. are obtained.

(b) benzyl 3-tert.butyldimethylsilyloxymethyl-4-hydroxybenzoate

To a solution of 2..7 g (10.5 mmoles) of benzyl 4-hydroxy-3-hydroxymethylbenzoate in 50 ml of DMF, there are added, successively, 1.47 ml (10.5 mmoles) of triethylamine and 51 mg (0.4 mmole) of 4-N,N-dimethylamino pyridine. The reaction medium is cooled to 0° C. and there is slowly added a solution of 1.6 g (10.5 mmoles) of tert.butyldimethylsilyl chloride in 20 ml of DMF. The mixture is stirred at ambient temperature for 8 hours. The reaction medium is poured into water and extracted with ethyl ether. The organic phase is decanted, dried on magnesium sulfate and evaporated. The resulting residue, which contains two products, is purified by chromatography on a silica column, by eluting with a 90:10 mixture of hexane and ethyl ether. 850 mg (23% yield) of benzyl 3-tert.butyldimethylsilyloxymethyl-4-hydroxybenzoate in the form of colorless oil and 930 mg (27% yield) of benzyl 4-tert.butyldimethylsilyloxy-3-hydroxymethylbenzoate in the form of a slightly yellow oil are obtained.

(c) benzyl 4-[3-(1-adamantyl)-4-methoxybenzoyloxy-] 3-tert.butyldimethylsilyloxymethyl benzoate In a manner analogous to Example 1(b), by reacting 2.2 g (7.25 mmoles) of 3-(1-adamantyl)-4-methoxybenzoyl chloride with 2.7 g (7.25 mmoles) of benzyl 3-tert.butyldimethylsilyloxymethyl-4-hydroxybenzoate, 3.1 g (71% yield) of the expected product in the form of colorless oil are obtained.

(d) benzyl 4-[3-(1-adamantyl)-4-methoxybenzoyloxy-] 3-hydroxymethylbenzoate

To a solution of 2.7 g (4.5 mmoles) of the ester obtained in Example 22(c) in 50 ml of THF, there are slowly added 5 ml of a molar solution of tetrabutylammonium fluoride in THF. The mixture is stirred for 30 minutes at ambient temperature. The reaction medium is poured into water and extracted with ethyl ether. The organic phase is decanted, dried on magnesium sulfate and evaporated. The resulting residue is purified by chromatography on a silica column eluted with dichloromethane. After evaporation of the solvent, 700 mg (30% yield) of the expected ester in the form of an opaque oil are obtained.

(e) 4-[3-(1-adamantyl)-4-methoxybenzoyloxy]-3 -hydroxymethylbenzoic acid

In a manner analogous to Example 15(e), starting with 700 mg (1.3 mmoles) of the preceding ester, 300 mg (55% yield) of 4-[3 -(1-adamantyl)-4-methoxybenzoyloxy]-3-hydroxymethyl benzoic acid having a melting point of 214°–216° C. are obtained.

Example 23

4-[3-(1-adamantyl)-4-methylthiobenzoyloxy]benzoic acid (a) methyl 3-(1-adamantyl)-4-(dimethylaminothiocarbonyloxy)benzoate Into a round bottom flask, there are introduced 2.4 g (0.08 mole) of sodium hydride (80% in oil) and 250 ml of DMF. Under a nitrogen current, there are slowly added 22.9 g (0.08 g mole) of methyl 3-(1-adamantyl)-4-hydroxybenzoate. The mixture is stirred until the cessation of gaseous emission. There are then added, all at once, 12.9 g (0.104 mole) of dimethylthiocarbamoyl chloride and the mixture is stirred for 16 hours at ambient temperature. The reaction medium is poured into water and extracted with ethyl ether. The organic phase is decanted, dried on magnesium sulfate and evaporated. The resulting residue is purified by chromatography on a silica column eluted with a 70:30 mixture of dichloromethane and hexane. After evaporation of the solvents, 1.8 g (63% yield) of the expected product having a melting point of 174°–175° C. are recovered.

(b) methyl 3-(1-adamantyl)-4-(dimethylaminocarbonylthio)benzoate 17.9 g (0.048 mole) of the preceding ester are heated under a nitrogen current at 300° C. for 15 minutes. The resulting residue is purified by chromatography on a silica column eluted with a 90:10 mixture of dichloromethane and hexane. After evaporation of the solvents, 14.2 g (80% yield) of the expected ester having a melting point of 150°–151° C. are recovered.

(c) 3-(1-adamantyl)-4-mercaptobenzoic acid

Into a round bottom flask there are introduced 14.2 g (38 mmoles) of the preceding ester and 200 ml of 2N methanolic soda. The mixture is heated at reflux for 4 hours. The reaction medium is evaporated to dryness. The residue is taken up in water, acidified to pH 1 with concentrated HCl, and extracted with ethyl ether. The organic phase is decanted, dried on magnesium sulfate and evaporated. 10.9 g of the crude acid, which will be used as such in the following synthesis, are recovered.

(d) methyl 3-(1-adamantyl)-4-methylthiobenzoate

Into a round bottom flask there are introduced 2.2 g (73 mmoles) of sodium hydride (80% in oil) and 50 ml of DMF. There is then slowly added a solution of 10.5 g (36.5 mmoles) of 3-(1-adamantyl)-4-mercaptobenzoic acid in 100 ml of DMF. The mixture is stirred until the cessation of gaseous emission. There are then added 5.7 ml (92 mmoles) of iodomethane and the mixture is stirred for 8 hours. The reaction medium is poured into water and extracted with ethyl ether. The organic phase is decanted, dried on magnesium sulfate and evaporated. The resulting residue is purified by chromatography on a silica column by eluting with a 40:60 mixture of dichloromethane and hexane. After evaporation of the solvents, 10 g (87% yield) of the expected ester having a melting point of 112°–113° C. are obtained.

(e) 3-(1-adamantyl)-4-methylthiobenzoic acid

In a manner analogous to Example 1(c), starting with 2 g (6.3 mmoles) of the preceding ester, 1.76 g (91% yield) of the expected acid having a melting point of 264°–265° C. are obtained.

(f) 3-(1-adamantyl)-4-methylthiobenzoyl chloride 1.7 g (5.6 mmoles) of 3-(1-adamantyl)-4-methylthiobenzoic acid and 20 ml of thionylchloride are heated at reflux until the cessation of gaseous emission. It is then evaporated to dryness and 1.8 g (100% yield) of the crude acid chloride, which is used as such for the following synthesis, are obtained.

(g) tert.butyl 4-[3-(1-adamantyl)-4-methylthiobenzoyloxy] benzoate

Into a round bottom flask, there are introduced 1 g (5.6 mmoles) of tert.butyl 4-hydroxybenzoate, 780 µl (5.6 mmoles) of triethylamine and 50 ml of THF. There are slowly added 1.8 g (5.6 mmoles) of the acid chloride prepared in Example 23(f) in 50 ml of THF. The mixture is stirred at ambient temperature for 8 hours. The reaction medium is poured into water and extracted with ethyl ether. The organic phase is decanted, dried on magnesium sulfate and evaporated. The resulting residue is purified by chromatography on a silica column eluted with a 60:40 mixture of dichloromethane and hexane. After evaporation of the solvents, 2.1 g (76% yield) of the expected ester having a melting point of 133°–134° C. are obtained.

(h) 4-[3-(1-adamantyl)-4-methylthiobenzoyloxy]benzoic acid

Into a round bottom flask, there are introduced 1.9 g (3.8 mmoles) of the preceding ester and 40 ml of carbon tetrachloride.

Under nitrogen there are slowly added 550 µl (3.8 mmoles) of iodotrimethylsilane and the mixture is stirred at ambient temperature for 3 hours. The reaction medium is poured into water and extracted with ethyl ether. The organic phase is decanted, dried on magnesium sulfate and evaporated. The resulting solid is recrystallized in ethyl acetate. After filtration and drying, 920 mg (57% yield) of 4-[3-(1-adamantyl)-4-methylthiobenzoyloxy]benzoic acid having a melting point of 276°–277° C. are obtained.

Example 24

4-[3-(1-adamantyl)-4-acetoxybenzoyloxy]benzoic acid (a) benzyl 4-[3-(1-adamantyl)-4-acetoxybenzoyloxy benzoate Into a round bottom flask there are introduced 66 mg (2.2 mmoles) of sodium hydride (80% in oil) and 5 ml of THF. There is slowly added a solution of 964 mg (2 mmoles) of benzyl 4-[3-(1-adamantyl)-4-hydroxybenzoyloxy]benzoate in 20 ml of THF. The mixture is stirred until the cessation of gaseous emission. There are then introduced 150 µl (2.2 mmoles) of acetyl chloride and the mixture is stirred at ambient temperature for 8 hours. The reaction medium is poured into water, and extracted with ethyl ether. The organic phase is decanted, dried on magnesium sulfate and evaporated. The resulting residue is purified by simple filtration on silica by eluting with dichloromethane. After evaporation of the solvent, 870 mg (83% yield) of the expected product having a melting point of 131°–132° C. are recovered.

(b) 4-[3-(1-adamantyl)-4-acetoxybenzoyloxy]benzoic acid

Into a reactor there are introduced 750 mg (1.4 mmoles) of the preceding ester, 100 mg of palladium on charcoal (10%) and 20 ml of dioxan. Hydrogenation is effected at ambient temperature and under a pressure of 6 bars for 2 hours. The catalyst is filtered and the filtrate is evaporated. The resulting residue is pulverized in the minimum of ethyl ether, filtered and dried. 500 mg (81% yield) of 4-[3-(1-adamantyl)-4-acetoxybenzoyloxy]benzoic acid having a melting point of 264°–265° C. are obtained.

Example 25

4-[3-(1-adamantyl)-4-methylsulfone benzoyloxy]benzoic acid (a) tert. butyl 4-[3-(1-adamantyl)-4-methylsulfonebenzoyloxy]benzoate Into a round bottom flask there are introduced 940 mg (1.9 mmoles) of tert. butyl 4-[3-(1-adamantyl)-4-methylthiobenzoyloxy]benzoate and 40 ml of dichloromethane. There are then added at 0° C., 700 mg (4 mmoles) of 3-chloroperoxybenzoic acid and the mixture is stirred at ambient temperature for 6 hours. The reaction medium is poured into water and extracted with ethyl ether. The organic phase is decanted, dried on magnesium sulfate and evaporated. The resulting residue is purified by chromatography on a silica column, eluted with ethyl ether. After evaporation of the solvent, 670 mg (67% yield) of the sulfone in the form of a slightly yellow oil are recovered.

(b) 4-[3-(1-adamantyl)-4-methylsulfonebenzoyloxy]benzoic acid

In a manner analogous to Example 23(h) starting with 630 mg (1.2 mmoles) of the preceding ester, 190 mg (35% yield) of 4-[3-(1-adamantyl)-4-methylsulfonebenzoyloxy]benzoic acid having a melting point of 248°–250° C. are obtained.

Example 26

4-[3-(1-adamantyl)-4-(carboxymethyleneoxy) benzoyloxy]benzoic acid (a) benzyl 4-[3-(1-adamantyl)-4-(benzyloxycarbonylmethyleneoxy)benzoyloxy]benzoate In a manner analogous to Example 24(a) by reacting 964 mg (2 mmoles) of benzyl 4-[3-(1-adamantyl)-4-hydroxybenzoyloxy]benzoate with 350 µl (2.2 mmoles) of benzyl 2-bromo acetate, 800 mg (63% yield) of the expected product having a melting point of 129°–130° C. are obtained.

(b) 4-[3-(1-adamantyl)-4-(carboxymethyleneoxy)benzoyloxy]benzoic acid

In a manner analogous to Example 21(b) starting with 750 mg (1.2 mmoles) of the preceding ester, 400 mg (75% yield) of the expected acid having a melting point of 287°–288° C. are obtained.

Example 27

4-[3-(1-adamantyl)-4-(2,3-dihydroxypropyloxy) benzoyloxy] benzoic acid (a) methyl 3-(1-adamantyl)-4-(2,2-dimethyl-1,3 -dioxolane-4-methyloxy)benzoate Into a three neck flask containing 10.0 g (34.9 mmoles) of 3-(1-adamantyl)-4-hydroxybenzoic acid and 5.31 g (38.4 mmoles) of potassium carbonate in 100 ml of DMF, there are slowly added 12.0 g (41.9 mmoles) of 2,2-dimethyl-1,3-dioxolane-4-methyltosylate in 75 ml of DMF. The mixture is stirred at 100° C. for 12 hours. The reaction medium is poured into ice water and extracted with 900 ml of ether. The organic phase is washed with water, dried on magnesium sulfate and evaporated. The resulting residue is chromatographed on silica by eluting with an 80:20 mixture of hexane and ethyl acetate which yields after evaporation of the solvents 8.82 g (63% yield) of methyl 3-(1-adamantyl)-4-(2,2 -dimethyl-1,3-dioxolane-4-methyloxy)benzoate having a melting point of 159° C.

(b) 3-(1-adamantyl)-4-(2,2-dimethyl-1,3 -dioxolane-4-methyloxy)benzoic acid

To a solution of 8.80 g (22 mmoles) of methyl 3-(1 -adamantyl)-4-(2,2-dimethyl-1,3-dioxolane-4-methyloxy) benzoate in 200 ml of methanol, there are added 16 g (0.4 mole) of soda. The mixture is heated at reflux for 3 ½ hours. The reaction medium is evaporated and the residue is taken up in 250 ml of water, then acidified to pH 3. The precipitate is extracted with 1.4 liters of ethyl ether. The organic phase is washed with water, dried on magnesium sulfate and evaporated. After pulverizing in hexane, 8.32 g (98% yield) of 3-(1-adamantyl)-4-(2,2-dimethyl-1,3-dioxolane-4-methyloxy)benzoic acid having a melting point of 224°–225° C. are isolated.

(c) allyl 4-[3-(1-adamantyl)-4-(2,2-dimethyl-1,3 -dioxolane-4-methyloxy)benzoyloxy]benzoate To a solution of 4.15 g (10.75 mmoles) of 3-(1-adamantyl)-4-(2,2-dimethyl-1,3-dioxolane-4-methyloxy)benzoic acid in 40 ml of dichloromethane, there are added 2.15 ml of dicyclohexylamine (10.8 mmoles) and the reaction is permitted to proceed for 1 hour at ambient temperature. There is then slowly added 0.85 ml (11.8 mmoles) of thionyl chloride. After stirring at ambient temperature for 4 hours, the medium is evaporated to dryness, and the residue is taken up in ethyl ether. The insolubles are removed by filtration and the filtrate is evaporated. The 3-(1 -adamantyl)-4-(2,2-dimethyl-1,3-dioxolane-4-methyloxy)benzoic acid thus obtained is placed in 30 ml of THF to which is then slowly added a solution, with stirring, containing 1.91 g (10.7 mmoles) of allyl 4-hydroxybenzoate, 1.65 ml (11.8 mmoles) of triethylamine and 13 mg of dimethylaminopyridine in 30 ml of THF. The reaction medium is stirred at ambient temperature under nitrogen for 20 hours and is then poured into ice water. This suspension is extracted with 600 ml of ethyl ether. The organic phase is then dried and evaporated. The residue is chromatographed on silica by eluting with dichloromethane to yield 4.24 g (72% yield) of allyl 4-[3-(1-adamantyl)-4-(2,2-dimethyl- 1,3-dioxolane-4-methyloxy)benzoyloxy]benzoate having a melting point of 106°–107° C.

(d) allyl 4-[3-(1-adamantyl)-4-(2,3-dihydroxypropyloxy) benzoyloxy benzoate 1.09 g (2 mmoles) of allyl 4-[3-(1-adamantyl)-4-(2,2 -dimethyl-1,3-dioxolane-4-methyloxy)benzoyloxy]benzoate are placed in 50 ml of dichloromethane and 3.80 g (20 mmoles) of paratoluene sulfonic acid are added. The reaction is left to proceed, with stirring, for 48 hours at ambient temperature. The medium is evaporated to dryness and the residue is taken up in 50 ml of dichloromethane. The organic phase is neutralized by washing with saturated NaHCO3, then rinsed with water, dried and evaporated. The residue is chromatographed on silica eluting with a 90:10 mixture of dichloromethane and ethyl ether thereby yielding 900 mg (89% yield) of allyl 4-[3-(1-adamantyl)-4-(2,3dihydroxypropyloxy) benzoyloxy]benzoate.

(e) 4-[3-(1-adamantyl)-4-(2,3-dihydroxypropyloxy) benzoyloxy]benzoic acid

To a solution of 891 mg (1.76 mmoles) of allyl 4-[3-(1 -adamantyl)-4-(2,3-dihydroxypropyloxy)benzoyloxy]benzoate in 15 ml of THF, there are added 102 mg (0,088 mmole) of tetrakis (triphenylphosphine) palladium (O). There is then slowly introduced a suspension consisting of 58 mg (1.93 mmoles) of sodium hydride (80% in oil) and 294 µl (1.93 mmoles) of ethyl malonate in 6 ml of THF. The mixture is stirred under nitrogen at ambient temperature for 1 hour and then evaporated to dryness. The solid is washed with 50 ml of ether, placed in 50 ml of water, acidified to pH 1 and extracted with 100 ml of ether. The organic phase is rinsed with water, dried on sodium sulfate and evaporated. The residue is recrystallized in ethyl acetate yielding 634 mg (72% yield) of 4-[3-(1-adamantyl)-4-(2,3dihydroxypropyloxy) benzoyloxy]benzoic acid having a melting point of 238°–239° C.

Example 28

4-[3-(1-adamantyl)-4-methoxycarbonylmethyloxy] benzoic acid (a) benzyl 4-[3-(1-adamantyl)-4-tert.butyldimethylsilyloxybenzoyloxy] benzoate 38.66 g (0.1 mole) of 3-(1-adamantyl)-4-tert. butyldimethylsilyloxy benzoic acid are converted to the acid chloride by the method previously described, then dissolved+in 140 ml of THF and slowly added to a suspension containing 1.66 g (0,055 mmoles) of NaH (80% in oil) and 1.41 g (0.05 mole) of benzyl 4-hydroxybenzoate in 5 ml of THF. The temperature is permitted to return to ambient temperature with stirring for 24 hours. The reaction medium is poured into ice water and extracted with ethyl ether. The organic phase is washed with water, dried on magnesium sulfate and evaporated. The residue is chromatographed on silica, eluting with a 40:60 mixture of dichloromethane and hexane yielding 28 g (47% yield) of benzyl 4-[3-(1-adamantyl)-4-tert.butyldimethylsilyloxy]benzoate having a melting point of 151°–152° C.

(b) benzyl 4-[3-(1-adamantyl)-4-hydroxybenzoyloxy]benzoate

A solution of 5.7 g (9.55 mmoles) of benzyl 4-[3-(1 -adamantyl)-4-tert.butyldimethylsilyloxybenzoyloxy]benzoate in 35 ml of THF is treated with 10.5 ml of tetrabutylammonium fluoride in 1M THF. The reaction medium is stirred at ambient temperature for 1 hour and then poured into ice water and extracted with 700 ml of ethyl ether. The organic phase is washed with 1N HCl, rinsed with water, dried on magnesium sulfate and evaporated. 4.60 g (100% yield) of benzyl 4-[3-(1-adamantyl)-4hydroxybenzoyloxy] benzoate having a melting point of 164°–165° C. are isolated.

(c) benzyl 4-[3-(1-adamantyl)-4-methoxycarbonylmethyloxy]benzoate 1.0 ml (10.2 mmoles) of methyl bromoacetate is slowly added to a solution of 4.49 g (9.3 mmoles) of benzyl 4-[3-(1-adamantyl)-4-hydroxybenzoyloxy]benzoate in 40 ml of DMF containing 309 mg (10.2 mmoles) of NaH (80% in oil). The reaction medium is left, with stirring, at ambient temperature overnight and then poured into ice water and extracted with 550 ml of ethyl ether. The organic phase is washed with water, dried on magnesium sulfate and evaporated. After chromatography on silica eluted with a 90:10 mixture of dichloromethane, 3.50 g (68% yield) of benzyl 4-[3-(1-adamantyl)-4methoxycarbonylmethyloxy]benzoate having a melting point of 123°–124° C. are isolated.

(d) 4-[3-(1-adamantyl)-4-methoxycarbonylmethyloxy]benzoic acid 3.46 g (6.24 mmoles) of benzyl 4-[3-(1-adamantyl)-4methoxycarbonylmethyloxy]benzoate in 50 ml of dioxan are hydrogenated under a pressure of 7 bars in the presence of 346 mg of Pd-C (10%) for 2 hours at 40° C. The reaction medium is filtered on kelite and evaporated, thereby yielding after recrystallization in ethyl acetate 2.55 g (88% yield) of 4-[3 -(1-adamantyl)-4-methoxycarbonylmethyloxy]benzoic acid having a melting point of 252°–253° C.

Examples of Composition

| A - Oral compositions | |
|---|---|
| (a) 0.2 g tablet | |
| 4-[3-(1-adamantyl)-4-methoxybenzoyloxy]-3-fluorobenzoic acid | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |
| (b) Drinkable suspension in 5 ml ampoule | |
| 4-[3-(1-adamantyl)-4-methoxybenzoyloxy]-2-fluorobenzoic acid | 0.001 g |
| Glycerine | 0.500 g |
| Sorbitol, 70% | 0.500 g |
| Sodium saccharinate | 0.010 g |
| Methyl parahydroxybenzoate | 0.040 g |
| Flavoring agent, sufficient amount | |
| Purified water, sufficient amount for | 5 ml |
| (c) 0.8 g tablet | |
| 4-[3-(1-adamantyl)-4-methoxybenzoyloxy]-2-hydroxybenzoic acid | 0.500 g |
| Pregelatinized starch | 0.100 g |
| Microcrystalline cellulose | 0.115 g |
| Lactose | 0.075 g |
| Magnesium stearate | 0.010 g |

In Example (c), 4-[3-(1-adamantyl)-4-methoxybenzoyloxy]-2-hydroxybenzoic acid can be replaced by 4-[5-(1-adamantyl)-2 -fluoro-4-methoxybenzoyloxy]benzoic acid.

| (d) Drinkable suspension in 10 ml ampoule | |
|---|---|
| 4-(3,5-di-tert.butyl-4-hydroxybenzoyloxy) benzoic acid | 0.200 g |

| -continued | |
|---|---|
| Glycerine | 1.000 g |
| Sorbitol, 70% | 1.000 g |
| Sodium saccharinate | 0.010 g |
| Methyl parahydroxybenzoate | 0.080 g |
| Flavoring agent, sufficient amount | |
| Purified water, sufficient amount for | 10 ml |
| B. Topical Compositions | |
| (a) Salve | |
| 4-[3-(1-adamantyl)-4-methoxybenzoyloxy]-3-fluorobenzoic acid | 0.020 g |
| Isopropyl myristate | 81.700 g |
| Fluid petrolatum oil | 9.100 g |
| Silica, sold under the trade name "AEROSIL 200" be Degussa | 9.180 g |
| (b) Salve | |
| 4-[3-(1-adamantyl)-4-methoxybenzoyloxy]-2-fluorobenzoic acid | 0.300 g |
| Codex white petrolatum, sufficient amount for | 100 g |
| (c) Nonionic water-in-oil cream | |
| 4-(3,5-di-tert.butyl-4-hydroxybenzoyloxy) benzoic acid | 0.100 g |
| Anhydrous eucerin | 39.900 g |
| Methyl parahydroxybenzoate | 0.075 g |
| Propyl parahydroxybenzoate | 0.075 g |
| Sterile demineralized water, sufficient amount for | 100 g |
| (d) Lotion | |
| 4-[3-(1-adamantyl)-4-methoxybenzoyloxy]-2-hydroxybenzoic acid | 0.100 g |
| PEG 400 | 69.900 g |
| Ethanol, 95% | 30.000 g |
| (e) Hydrophobic salve | |
| 4-[5-(1-adamantyl)-2-fluoro-4-methoxybenzoyloxy] benzoic acid | 0.300 g |
| Isopropyl myristate | 36.400 g |
| Silicone oil, sold by Rhone Poulenc under the trade name "Rhodorsil 47 V 300" | 36.400 g |
| Beeswax | 13.600 g |
| Silicone oil, sold by Goldschmidt under the trade name "Abil 300.000 cst", sufficient amount for | 100 g |
| (f) Nonionic oil-in-water cream | |
| 4-[3-(1-adamantyl)-4-methoxybenzoyloxy]-3-fluorobenzoic acid | 1.000 g |
| Cetyl alcohol | 4.000 g |
| Glycerol monostearate | 2.500 g |
| PEG 50 stearate | 2.500 g |
| Karite butter | 9.200 g |
| Propylene glycol | 2.000 g |
| Methyl parahydroxybenzoate | 0.075 g |
| Propyl parahydroxybenzoate | 0.075 g |
| Sterile demineralized water, sufficient amount for | 100 g |
| C. Administration by injection | |
| 3 ml injectable ampoule | |
| 4-[3-(1-adamantyl)-4-methoxybenzoyloxy]-2-hydroxy benzoic acid, micronized | 0.003 g |
| Water for injectable preparation, sufficient amount for | 3 ml |

What is claimed is:

1. A bi-aromatic ester having the formula

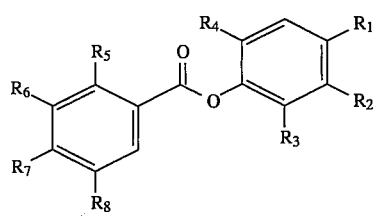

wherein $R_1$ represents hydrogen, OH, —$CH_3$, —$CH_2OH$, —$CH(OH)CH_3$,

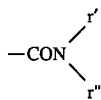

or $SO_2R_{10}$, $R_{10}$ represents OH, alkyl having 1–6 carbon atoms or

r' and r" represent hydrogen, alkyl having 1–6 carbon atoms, aryl, aralkyl, monohydroxyalkyl or polyhydroxyalkyl, or r' and r" taken together form a heterocycle, $R_2$ represents hydrogen, alkyl having 1–6 carbon atoms, $OR_9$, fluorine or —$CF_3$, $R_9$ represents hydrogen, alkyl having 1–6 carbon atoms, monohydroxyalkyl or polyhydroxyalkyl, $R_3$, $R_4$ and $R_5$ represent hydrogen, fluorine, OH, —$CH_3$, —$OCH_3$ —$CF_3$, —COOH or —$CH_2OH$, $R_6$ and $R_8$ represent hydrogen, α-substituted alkyl having 3–15 carbon atoms, α,α'-disubstituted alkyl having 4–12 carbon atoms, cycloalkyl having 3–12 carbon atoms, mono- or polycyclic cycloalkyl having 5–12 carbon atoms whose linking carbon is trisubstituted, —$SR_{11}$, —$SO_2R_{11}$ or —$SOR_{11}$, $R_{11}$ represents alkyl having 1–6 carbon atoms or cycloalkyl, with the proviso that $R_6$ and $R_8$ do no simultaneously represent hydrogen, $R_7$ represents hydrogen, alkyl having 1–6 carbon atoms, alkenyl, alkenyloxy, $OR_{12}$ or $SR_{13}$, $SOR_{14}$ or $SO_2R_{14}$, $R_{12}$ represents hydrogen, alkyl having 1–6 carbon atoms, alkenyl, monohydroxyalkyl, polyhydroxyalkyl or —$(CH_2)_n$—$COR_{15}$, wherein n is 0.1 or 2, and $R_{15}$ represents hydrogen, OH, alkyl having 1–6 carbon atoms or alkoxy having 1–6 carbon atoms, $R_{13}$ represents hydrogen, alkyl having 1–6 carbon atoms or aralkyl, $R_{14}$ represents OH, alkyl having 1–6 carbon atoms or aralkyl, with the proviso that when $R_1$ represents —$CH_2OH$, —$CH(OH)CH_3$,

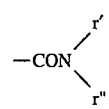

and $R_2$ represents hydrogen, then:
 (i) either $R_3$ and $R_4$ are other than hydrogen or —$CH_3$,
 (ii) or $R_7$ is other than $OR_{12}$ and $R_6$ or $R_8$ is cycloalkyl having more than 7 carbon atoms,
 (iii) or $R_7$ represents $OR_{12}$, but $R_6$ and $R_8$ are other than hydrogen,
 (iv) or $R_7$ represents $OR_{12}$ but $R_5$ is other than hydrogen.

2. The compound of claim 1 selected from the group consisting of
4-[3-(1-adamantyl)-4-methoxybenzoyloxy]benzenesulfonamide, 4-hydroxyphenyl-3-(1-adamantyl)-4-methoxybenzoate,
phenyl 3-(1-adamantyl)-4-methoxybenzoate and
4-methylphenyl 3-(1-adamantyl)-4-methoxybenzoate.

3. The compound of claim 1 in the form of an alkali metal salt, an alkaline earth metal salt, a zinc salt or an organic amine salt.

4. The compound of claim 1 wherein said alkyl having 1–6 carbon atoms is selected from the group consisting of methyl, ethyl, isopropyl, butyl and tert.butyl.

5. The compound of claim 1 wherein said α-substituted alkyl is selected from the group consisting of 1-methyl propyl, 1-ethyl propyl, 1-methyl hexyl, 1-methyl decyl and 1-ethyl dodecyl.

6. The compound of claim 1 wherein said α,α'-disubstituted alkyl is selected from the group consisting of tert.butyl, 1,1-dimethyl propyl, 1-methyl-1-ethyl propyl, 1-methyl-1-ethyl hexyl and 1,1-dimethyl decyl.

7. The compound of claim 1 wherein said monohydroxyalkyl is 2-hydroxyethyl, 2-hydroxypropyl or 3-hydroxypropyl.

8. The compound of claim 1 wherein said polyhydroxyalkyl has 3–6 carbon atoms and 2–5 hydroxyl groups.

9. The compound of claim 8 wherein said polyhydroxyalkyl is 2,3-dihydroxypropyl, 2,3,4-trihydroxybutyl, 2,3,4,5-tetrahydroxypentyl or the residue of pentaerythritol.

10. The compound of claim 1 wherein said alkenyl having 2–6 carbon atoms is vinyl, allyl or 2-butenyl.

11. The compound of claim 1 wherein said aryl is phenyl or phenyl substituted by at least one of halogen, hydroxyl or nitro.

12. The compound of claim 1 wherein said aralkyl is benzyl or phenethyl, optionally substituted by at least one of halogen, hydroxyl or nitro.

13. The compound of claim 1 wherein said mono or polycyclic cycloalkyl having 5–12 carbon atoms whose linking carbon is trisubstituted is 1-methylcyclohexyl or 1-adamantyl.

14. The compound of claim 1 wherein r' and r" taken together form a heterocycle selected from the group consisting of piperidino, morpholino, pyrrolidino, piperazino and piperazino substituted in the 4 position by $C_1$–$C_6$ alkyl, monohydroxyalkyl or polyhydroxyalkyl.

15. A pharmaceutical composition comprising in a pharmaceutical acceptable vehicle suitable for enteral, parenteral, topical or ocular administration to an animal or man, at least one compound of formula (I) of claim 1.

16. The composition of claim 15 wherein said compound of formula (I) is present in an amount ranging from 0.0001 to about 5 percent by weight based on the total weight of said composition.

17. A method for the treatment of a dermatologic, rheumatismal, respiratory or ophthalmologic ailment comprising administering to an animal or a person suffering from said ailment an effective amount of the composition of claim 15.

18. A cosmetic composition for body and hair hygiene comprising in a cosmetically acceptable vehicle at least one compound of formula (I) of claim 1.

19. The composition of claim 18 wherein said compound of formula (I) is present in an amount ranging from 0.0001 to 1 percent by weight based on the total weight of said composition.

20. The composition of claim 18 wherein said compound of formula (I) is present in an amount ranging from 0.001 to 0.01 percent by weight based on the total weight of said composition.

* * * * *